US006764581B1

(12) United States Patent
Forrow et al.

(10) Patent No.: US 6,764,581 B1
(45) Date of Patent: *Jul. 20, 2004

(54) ELECTRODE WITH THIN WORKING LAYER

(75) Inventors: Nigel J. Forrow, Abingdon (GB); Simon W. Bayliff, Abingdon (GB)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/924,267

(22) Filed: Sep. 5, 1997

(51) Int. Cl.[7] ............................................. G01N 27/327
(52) U.S. Cl. ........................... 204/403.14; 204/403.04
(58) Field of Search .................. 435/817; 204/403, 204/415, 403.04, 403.09, 403.1, 403.11, 403.14, 403.13; 205/777.5, 778, 793

(56) References Cited

U.S. PATENT DOCUMENTS

| | | | |
|---|---|---|---|
| 5,082,550 A | * 1/1992 | Rishpon et al. | 204/403 |
| 5,160,418 A | * 11/1992 | Mullen | 204/153.12 |
| 5,183,742 A | * 2/1993 | Omoto et al. | 435/14 |
| 5,494,562 A | * 2/1996 | Maley et al. | 204/403 |
| 5,628,890 A | 5/1997 | Carter et al. | 204/403 |
| 5,658,443 A | * 8/1997 | Yamato et al. | 204/403 |
| 5,708,247 A | * 1/1998 | McAleer et al. | 204/403 |
| 5,798,031 A | 8/1998 | Charlton et al. | |
| 5,804,047 A | * 9/1998 | Karube et al. | 204/403 |

FOREIGN PATENT DOCUMENTS

| | | |
|---|---|---|
| EP | 0 230 472 | 8/1987 |
| EP | 0 351 891 | 1/1990 |
| EP | 0 690 134 | 1/1996 |
| JP | 3202764 A * | 9/1991 |
| WO | 95 22597 | 8/1995 |

OTHER PUBLICATIONS

Gooding et al. ("An enzyme electrode with response independent of the thickness of the enzyme layer", Sens. Actuators, B (1996), B34(1–3), 516–523), 1996.*

Caplus abstract of arai et al. ("Production process of glucose sensor by printing method", Chem. Ses. (1996), 12 (Suppl. a), 137–140), 1996.* e–mail from PTO reference librarian stating the pubication date of Chemical Sensors vol. 12, Supplement A, which contains Arai article, Jan. 2000.*

JPO abstract of Kawaguri et al. (JP 03202764 A), Sep. 1991.*

* cited by examiner

Primary Examiner—Alex Noguerola
(74) Attorney, Agent, or Firm—David L. Weinstein

(57) ABSTRACT

Disclosed is an improved electrode for use in an electrochemical sensor for measuring an analyte in a sample. The electrode includes a thin working layer whose thickness is from 2 to 10 microns. Also disclosed is an electrode strip that includes an electrode with a thin working layer. Typically, the thin working layer includes an enzyme and a redox mediator. In an electrode for measuring glucose, the enzyme can be glucose oxidase and the redox mediator can be ferrocene.

12 Claims, 3 Drawing Sheets

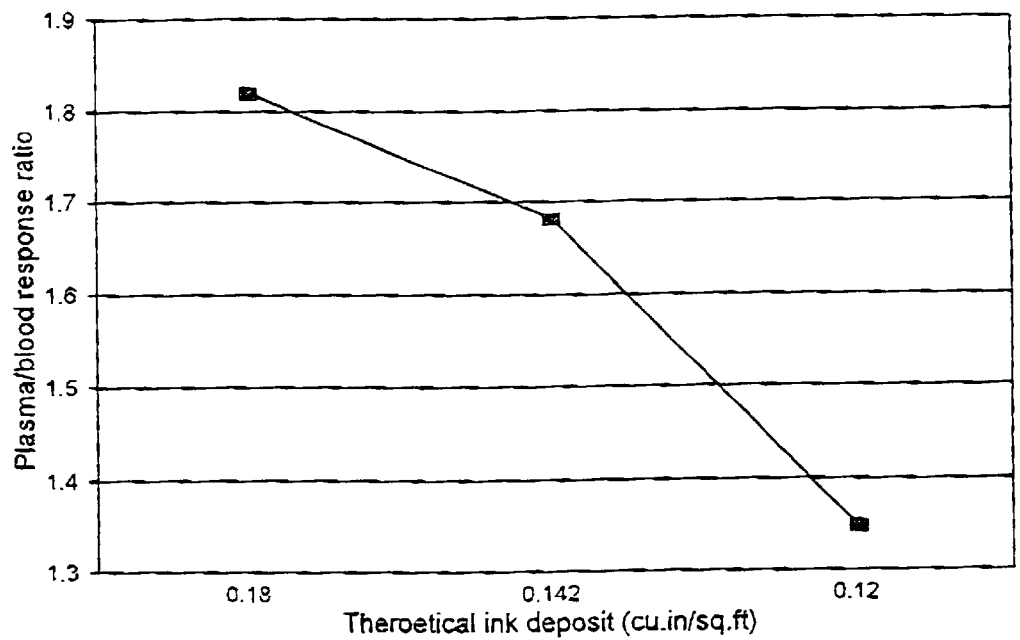

US 6,764,581 B1

ELECTRODE WITH THIN WORKING LAYER

FIELD OF THE INVENTION

The invention relates to electrochemical sensors, biomedical testing, and blood analysis.

BACKGROUND OF THE INVENTION

Electrochemical assays for determining the concentration of enzymes or their substrates in complex liquid mixtures have been developed. For example, electrochemical sensor strips have been developed for the detection of blood glucose levels. Electrochemical sensor strips generally include an electrochemical cell in which there is a working electrode and a reference electrode. The potential of the working electrode typically is kept at a constant value relative to that of the reference electrode.

Electrochemical sensor strips are also used in the chemical industry and food industry, to analyze complex mixtures. Electrochemical sensors are useful in biomedical research, where they can function as invasive probes, and for external testing (i.e., testing of blood obtained by a needle and syringe, or a lance).

Typical electrochemical sensors for blood analysis measure the amount of analyte in a blood sample by using a working electrode coated with a layer containing an enzyme and a redox mediator and a reference electrode. When the electrodes contact a liquid sample containing a species for which the enzyme is catalytically active, the redox mediator transfers electrons in the catalyzed reaction. When a voltage is applied across the electrodes, a response current results from the reduction or oxidation of the redox mediator at the electrodes. The response current is proportional to the concentration of the substrate. Some sensors include a dummy electrode coated with a layer containing the redox mediator but lacking the enzyme. The response current at the dummy electrode represents a background response of the electrode in contact with the sample. A corrected response is derived by subtracting the response of the dummy electrode from the response of the working electrode. This dummy subtraction process substantially eliminates background interferences, thereby improving the signal-to-noise ratio in the electrode system.

SUMMARY OF THE INVENTION

The invention features an electrode for use in an electrochemical sensor for measuring an analyte in a sample. The electrode includes a thin working layer. The thin working layer can be from 2 to 10 microns thick, and preferably is from 4 to 8 microns thick. Preferably, the thin working layer includes an enzyme and a redox mediator. Preferably, it also includes a binder, a film former, and a filler. In an electrode for measuring glucose, the enzyme uses glucose as a substrate, and preferably the enzyme is glucose oxidase or glucose dehydrogenase. Preferably, the thin working layer includes a redox mediator such as ferrocene, a ferrocene derivative, ferricyanide, or an osmium complex. The thin working layer of the electrode can be a printed layer, for example, a screen printed layer.

The invention also features an electrode strip for use in an electrochemical sensor for measuring an analyte in a sample. The electrode strip includes an electrode, which includes a thin working layer. The thin working layer can have a thickness of 2 to 10 microns. Preferably, the thickness is 4 to 8 microns. The thin working layer preferably includes an enzyme and a redox mediator. Preferably, it also includes a binder, a film former, and a filler. In an electrode strip for measuring glucose, the enzyme uses glucose as a substrate, and preferably the enzyme is glucose oxidase or glucose dehydrogenase. Preferably, the thin working layer includes a redox mediator such as ferrocene, a ferrocene derivative, ferricyanide, or an osmium complex. The thin working layer of the electrode can be a printed layer, for example, a screen printed layer. The electrode arrangement in the electrode strip can include a working electrode, a dummy electrode, and a reference electrode. Preferably, the reference electrode is downstream of the working electrode, relative to sample flow. The electrode strip can also include a hydrophilic mesh layer overlaying a sample loading area and the electrode arrangement. In addition, the electrode strip can include a cover layer defining an upper boundary of a cell volume encompassing the electrode arrangement, and an aperture in the cover layer, above the sample loading area.

BRIEF DESCRIPTION OF THE DRAWINGS

FIG. 5 is graph of plasma/blood response ratio plotted against theoretical ink deposit (cu.in./sq.ft.).

DESCRIPTION OF THE PREFERRED EMBODIMENTS

Figure 1:
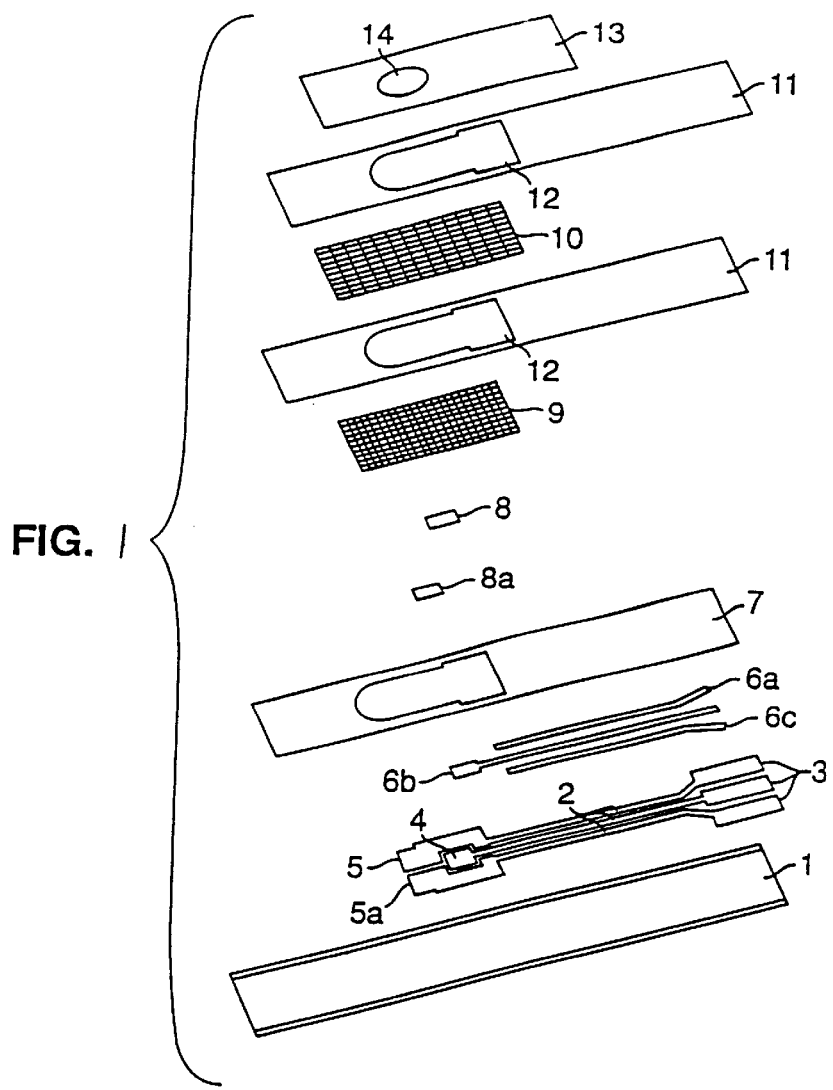
FIG. 1 is an exploded view of an electrode strip according to one embodiment of the invention.

The precision and accuracy of analyte measurements using an electrode sensor strip are improved by using electrodes with a thin working layer. The thin working layer has a thickness between about 2 microns and about 10 microns. Preferably, it has a thickness between about 4 and about 8 microns. As used herein, "working layer" means a layer that contains electrochemical assay reaction components and forms a slurry with a sample.

The performance of an electrode strip depends, in part, on its calibration slope. In general, electrochemical performance improves as its calibration slope increases. This is because the signal-to-noise ratio increases as the slope increases, and consequently, precision and accuracy are improved. This is particularly true at low analyte levels, where noise is significant.

In printed electrode sensor strips, the calibration slope depends on the electrochemical activity of the printed layer on the surface of the working electrode. The electrochemical activity depends on the rate of dissolution and/or resuspension of the printed layer, upon contact with a sample.

The ink used to form the thin working layer on the working electrode includes an enzyme that uses the analyte as a substrate. The ink used to form the thin working layer on the dummy electrode does not include the enzyme. When the analyte is glucose, the enzyme is preferably glucose oxidase, and the ink contains from about 70 to about 700 glucose oxidase activity units/g of ink.

The ink used to form the thin working layer on the working electrode and dummy electrode includes a redox mediator. The redox mediator can be any electrochemically active compound that accepts or donates electrons to the enzyme. Examples of redox mediators are ferrocene, ferrocene derivatives, ferricyanide, and osmium complexes.

The ink can include a binder. The binder can be a polysaccharide. Suitbable polysaccharides include guar gum, alginate, locust bean gum, carrageenan, and xanthan.

The ink can include an enzyme stabilizer. Examples of enzyme stabilizers are glutamate, trehalose, aspartate, DEAE dextran, lactitol, gelatin, and sucrose. A suitable range for stabilizer concentration is about 2 to about 11 weight percent, with about 5 weight percent being preferred.

The ink can include a film former. Suitable film formers include polyvinyl alcohol (PVA), polyvinyl pyrrole, cellulose acetate, carboxymethylcellulose, poly (vinyl oxazolidinone).

The ink can include a filler. The filler can be conducting or nonconducting. Suitable fillers include graphite, titanium dioxide, silica, and alumina. Preferably, the filler is a carbonaceous conductor.

The ink can include a defoaming agent. Suitable defoaming agents include a blend of non-ionic fats, an oil, a wax, and a synthetic non-ionic surfactant block co-polymer of propylene oxide and ethylene oxide.

The ink can include a pH buffer. Suitable pH buffers include imidazole, HEPES, PBS, and the like. Preferably, the buffer is adjusted to about pH 7.5.

An electrode strip suitable for a thin printed working layer according to this invention is described in Carter et al., U.S. Pat. No. 5,628,890, which is incorporated herein by reference. An electrode strip suitable for a thin printed working layer according to this invention is illustrated in FIGS. 1 and 2.

Figure 2:
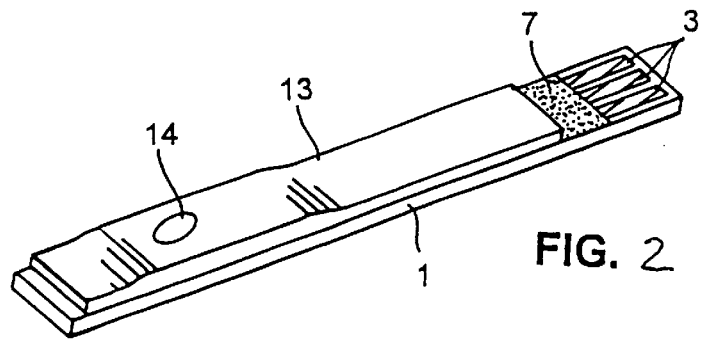
FIG. 2 is a perspective view of the assembled strip of FIG. 1

Referring to FIGS. 1 and 2, an electrode support 1, typically made of PVC, polycarbonate, or polyester, supports three printed tracks of electrically conducting carbon ink 2. The printed tracks 2 define the positions of the working electrode 5, dummy electrode 5a, reference electrode 4, and electrical contacts 3. The contacts 3 fit into a compatible meter (not shown).

The elongated portions of the printed tracks 2 of electrically conducting carbon ink are each overlaid with a silver/silver chloride particle track 6a, 6b, and 6c. Except for the electrode areas, the silver/silver chloride particle tracks 6a, 6b, 6c are overlaid with a layer of hydrophobic, electrically insulating material 7. The hydrophobic electrically insulating material is useful to surround the area containing the electrode arrangement. Hydrophobicity of the electrically insulating material is useful for confining the sample to the area containing the electrode arrangement. A preferred electrically insulating material is Sericol™ (Sericol Ltd., Broadstairs, Kent, UK).

The thin working areas of the electrodes 8, 8a are formed from the ink described above. The ink is deposited on electrode areas 5, 5a of carbon tracks 2. Preferably, the ink is deposited by a conventional printing technique, e.g., screen printing, lithography, gravure, and flexographic printing. Screen printing is particularly preferred.

Referring to FIG. 1, two surfactant coated mesh layers 9, 10 overlay the electrodes 4, 5, 5a. The mesh layers protect the printed components from physical damage. They also facilitate wetting of the electrodes by the aqueous sample. Finely woven nylon is suitable for the mesh layers. Alternatively, any woven or non-woven material can be used. For a detailed discussion of the mesh layers see Carter et al., U.S. Pat. No. 5,628,890, which is herein incorporated by reference.

If the mesh material is hydrophobic (e.g., nylon or polyester), it is coated with a surfactant. If a hydrophilic mesh is used, the surfactant coating can be omitted. Hydrophilicity of the mesh allows the sample to wick along the mesh layer to the electrodes. The wicking properties of the mesh can be controlled by changing the type or amount of surfactant on the mesh material. Various surfactants are suitable for coating the mesh material. A preferred surfactant is FC 170C FLUORAD™ fluorochemical surfactant (3M, St. Paul, Minn.). FLUORAD™ is a solution of a fluoroaliphatic oxyethylene adduct, lower polyethylene glycols, 1,4-dioxane, and water. A preferred surfactant loading for most applications is from about 15–20 µg/mg of mesh (e.g., about 1.0 percent w/w). The preferred surfactant loading will vary depending on the type of mesh and surfactant used and the sample to be analyzed. It can be determined empirically by observing flow of the sample through the mesh with different levels of surfactant. In general, a loading of 1–10 µg/mg of mesh is preferred.

The upper mesh layer 10 helps to control the influx of sample as it travels from the sample application area toward the electrode arrangement. The upper mesh layer 10 does so by providing a space to accomodate air displaced by the sample. Spacing of the relatively large filaments in the upper mesh layer 10, perpendicular to the direction of sample flow, helps to control the sample flow by presenting repeated physical barriers to the movement of the sample, as it travels along the sample transfer path.

Preferably, the upper mesh layer 10 is woven, and is coarser than the lower mesh layer 9. Preferably, the thickess of the upper mesh layer is between about 100 microns and about 1000 microns. More preferably, it is from about 100 to about 150 microns.

The mesh layers 9, 10 are held in place by a dielectric coating 11, which impregnates the periphery of the mesh layers 9, 10. The dielectric coating 12 can be applied by screen printing. The dielectric coating 12 covers no portion of the electrodes 4, 5, 5a. Preferably, the dielectric coating is hydrophobic, so that it efficiently confines the sample. Preferably, the hydrophobic dielectric coating is POLYPLAST™ (Sericol Ltd., Broadstairs, Kent, UK). More preferably, it is SERICARD™ (Sericol).

The uppermost layer on the electrode strip is a cover layer 13. Preferably, the cover layer 13 is substantially impermeable. A suitable material for formation of the cover layer 13 is a flexible polyester tape.

The cover layer 13 defines an upper boundary of the electrochemical cell volume, and thus, it determines the maximum depth of the aqueous sample. The cover layer 13 fixes the upper boundary of the cell volume at a predetermined height, which depends on the thickness of the mesh layers 9, 10. The cell height, and thus maximum sample depth, is selected to ensure a suitably high solution resistance.

The cover layer 13 has an aperture 14 for sample access to the underlying mesh layers 9, 10. The aperture 14 is located over a sample loading area, which is adjacent to the upstream ends of the working electrode 5 and dummy electrode 5a. The aperture 14 can be of any suitable size large enough to allow sufficient volume of sample to pass through to the mesh layers 9, 10. It should not be so large as to expose any portion of the electrodes 4, 5, 5a. The aperture 14 can be formed in the cover layer 13 by any suitable method, e.g., die punching.

Cover layer 13 is peripherally affixed to the strip by means of a suitable adhesive. Preferably, the cover layer 13 is affixed by means of a hot melt adhesive. The hot melt adhesive typically has a coating weight between 10 and 50 g/M², preferably from 20 to 30 g/m². Pressure sensitive adhesives or other suitable adhesives can also be used. When a heat sensitive dielectric coating 11 is used, e.g., SERICARD™, heat welding of the cover layer 13 should be carried out in a manner that does not damage the dielectric coating 11.

Optionally, the upper surface of the cover layer 32 can be coated with a layer of silicone or other hydrophobic coating. This helps to drive the applied sample onto the hydrbphlic mesh layers 9, 10, thus facilitating the application of small volumes.

Referring to FIG. 2, an electrode strip of the invention is connected, via electrode contacts 3, to a compatible meter (not shown), and then a sample is placed in aperture 14.

Any of various known methods can be used to produce a thin working layer according to this invention. For example, the thin working layer can be screen printed, using a suitable electrode printing ink. When the thin working layer is applied by screen printing, layer thickness can be controlled by screen mesh size. For example, with a suitable ink, a screen mesh size of 400 can be used to produce a thin working layer of 2 to 10 microns. A suitable ink for screen printing a thin working layer is a low viscosity ink. Viscosity can be adjusted using methods well known in the art. When screen printing is used, working layer thickness also can be controlled by adjusting the thickness of the screen emulsion. The amount of ink deposited, i.e., print thickness, also can be controlled by adjusting other printer parameters, such as breakaway/snap-off distance, squeegee pressure, squeegee speed and squeegee durometer (hardness).

The following examples are intended to be illustrative of, and not limiting to, the invention.

EXAMPLE 1

Figure 3:
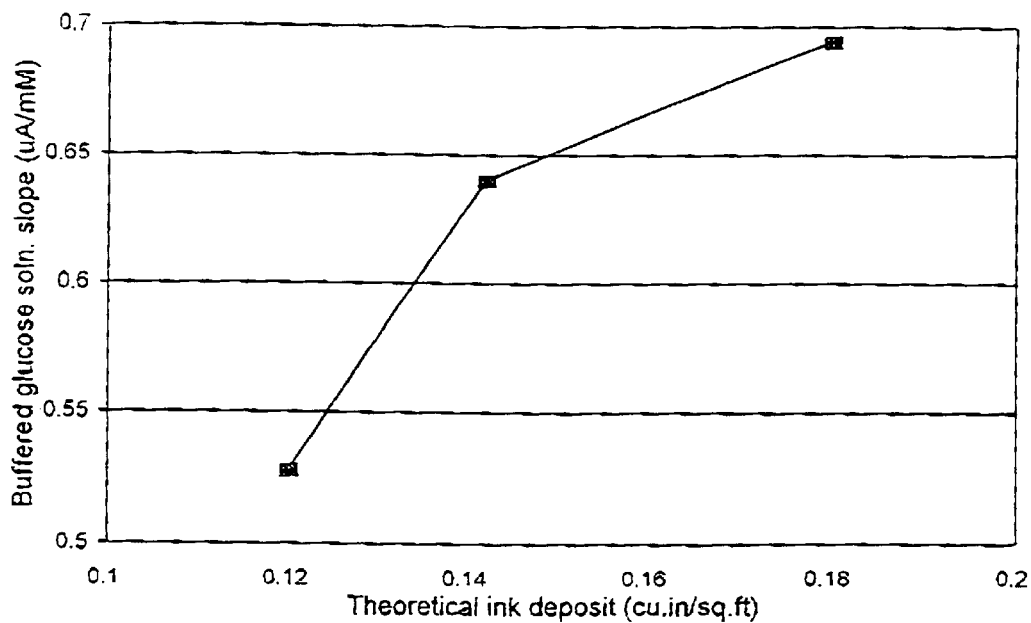
FIG. 3 is a graph of buffered glucose solution calibration slope ($\mu$A/mM) plotted against theoretical ink deposit (cu.in./sq.ft.).

Dependence of Buffered Glucose Calibration Slope on Print Thickness of Electrode Working Area Electrode strips were constructed essentially as described in U.S. Pat. No. 5,628,890, using different working electrode inks and print screens with 250, 325, or 400 mesh size. Buffered solutions containing known glucose concentrations were prepared. Aliquots of these standard solutions were applied to the electrode strips, and steady state responses were obtained using a compatible meter system. Calibration slopes were calculated as $\mu A$ current per mM glucose. FIG. 3 shows the electrode response slope ($\mu A$/mM), measured with buffered glucose solutions.

Referring to FIG. 3, the calibration slope for a buffer standard solutions of analyte, i.e., glucose, decreased as the theoretical volume of ink decreased. The reduction in current response correlated with the reduction in total amount of assay components, as working area layer thickness decreased.

EXAMPLE 2

Figure 4:
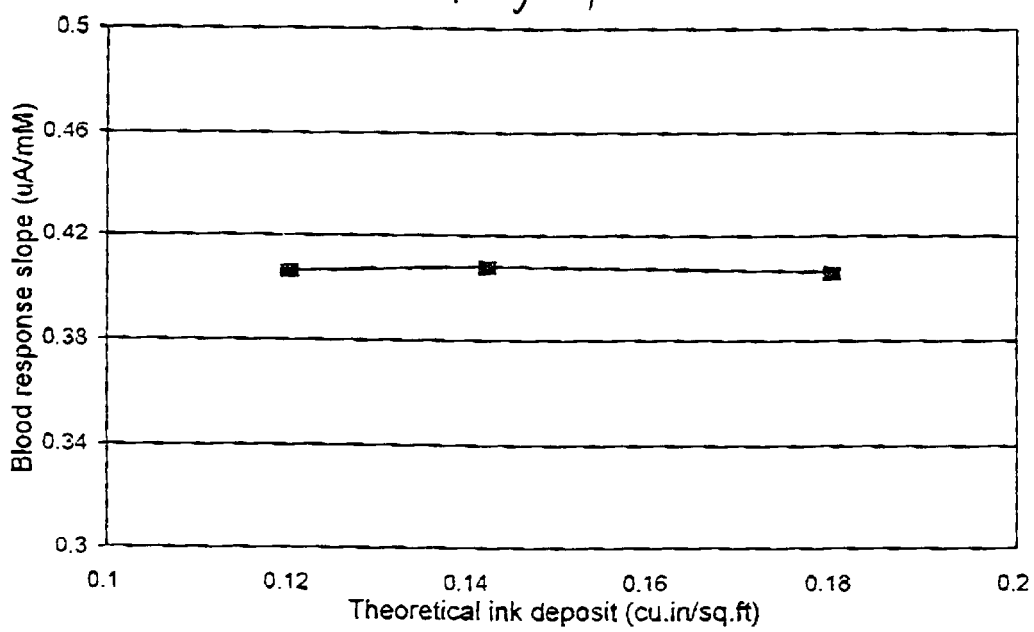
FIG. 4 is a graph of blood glucose calibration slope ($\mu$A/mM) plotted against theoretical ink deposit (cu.in./sq.ft.).

Dependence of Blood Glucose Calibration Slope on Print Thickness of Electrode Working Area Electrode strips were produced as in Example 1. Known amounts of glucose were added to anticoagulated venous blood samples. Aliquots of these samples were applied to the electrode strips, and steady state responses were obtained using a compatible meter system. Calibration slopes were calculated as $\mu A$ current per mM glucose. FIG. 4 shows the electrode response slope ($\mu A$/mM), measured with spiked venous blood. Surprisingly, the response remained essentially constant as the theoretical working electrode working area print thickness decreased. This contrasted with the result observed with glucose control solutions, and this result was not predicted from conventional electrochemical theory.

EXAMPLE 3

Relationship Between Electrode Working Area Print Thickness and Electrode Response to Glucose in Venous Blood and Plasma Electrode strips were produced as in Examples 1 and 2. Anticoagulated venous blood samples were divided into two aliquots. Red blood cells were removed from one aliquot by conventional means and discarded. Samples of plasma and whole blood were applied to the electrode strips, and steady state responses were obtained using a compatible meter system. The ratios of the electrode responses ($\mu A$) in plasma and whole blood were calculated and plotted against theoretical ink deposition (electrode working area print thickness) in FIG. 5. The ratio of the plasma and whole blood response indicated the sensitivity of the electrodes to sample hematocrit. As the ratio approached 1.0, the sensor response was less dependent on the sample hematocrit. FIG. 5 shows that the plasma/blood ratio, and therefore the hematocrit sensitivity of the sensor, was reduced as the electrode working area print thickness decreased. The reduction in red cell fouling improved the precision and accuracy of the measurement system for whole blood analysis.

EXAMPLE 4

Print Thickness Measurements Using Using Sloan Dektak II Profilometer

The thicknesses of ink deposits (electrode thin working layers) on electrode strips of this invention, manufactured under standard conditions, were determined by profilometric measurements. Similar measurements were carried out on comparable ink deposits printed on glass. For comparison, corresponding measurements were performed on prior art electrode strips (Medisense G2a strips).

All profilometry measurements were made using a Sloan Dektak II Profilometer at the AEA Science and Technology Centre, Harwell, U.K. Samples were measured in triplicate. The working ink print areas of G2a (prior art) strips and G2b strips were exposed by removing the nylon mesh prior to measurements. Samples of G2a and G2b inks were also printed directly onto a glass substrate (using standard manufacturing procedures and equipment). G2a inks were printed using 325 mesh and G2b using 400 mesh screen sizes.

G2a print thickness on strips ranged from 5.8 to 10.4 $\mu$m. It was not possible to record the thickness of G2b ink on strip samples even though the profilometer is able to detect height differences over 0.1 $\mu$m. This indicates that the G2b ink deposit was less than 1 $\mu$m in thickness, or that the ink embedded into the underlying carbon track during printing. Measurements showed the carbon track on G2a strips to be approximately 20 $\mu$m thick. The measured thickness of the carbon track plus working area ink on G2b strips was only about 16 $\mu$m. This indicated that the carbon track on the G2b strip had been exposed to a greater level of compression during manufacture.

When printed onto a glass substrate, the G2a working area print thickness was measured at 14 $\mu$m. The G2b working area print was measured at 8 $\mu$m. The use of glass in this comparative test substantially eliminated measurement error caused by embedding of ink into the surface onto which the ink was printed. These test results indicated that the thin working layer according to this invention was substantially thinner than prior art working area layers, even though direct measurement of layer thickness can be complicated by embedding of ink into the electrode support.

Other embodiments are within the following claims.

We claim:

1. A sensor for measuring glucose in a sample of blood, said sensor comprising an electrode arrangement, which comprises an electrode support having at least one printed track of electroconductive carbon ink, said at least two printed tracks defining the positions of at least two electrodes, one of said at least two electrodes comprising a thin working layer, said thin working layer having a thickness in the range of 2 to 10 microns, said thin working layer comprising a printed ink, said ink comprising an enzyme and a redox mediator, the other of said at least two electrodes being a reference electrode, said sensor, in the presence of a sample of blood, having a response slope that remains substantially constant in said thickness range.

2. The sensor of claim 1, wherein said thin working layer has a thickness of 4 to 8 microns.

3. The sensor of claim 1, wherein said thin working layer further comprises a binder, a film former, and a filler.

4. The sensor of claim 1, wherein said enzyme uses glucose as a substrate for said enzyme.

5. The sensor of claim 4, wherein said enzyme is selected from the group consisting of glucose oxidase and glucose dehydrogenase.

6. The sensor of claim 1, wherein said redox mediator is selected from the group consisting of ferrocene, a ferrocene derivative, ferricyanide, and an osmium complex.

7. The sensor of claim 1, wherein said thin working layer is a screen printed layer.

8. The sensor of claim 1, wherein said electrode arrangement comprises a working electrode, a dummy electrode, and a reference electrode.

9. The sensor of claim 8, said reference electrode is downstream of said working electrode, relative to direction of sample flow.

10. The sensor of claim 1, further comprising a hydrophilic mesh layer overlaying a sample loading area and said electrode arrangement.

11. The sensor of claim 10, further comprising a cover layer defining an upper boundary of a cell volume encompassing said electrode arrangement, and an aperture in said cover layer, said aperture located above said sample loading area.

12. The sensor of claim 1, wherein said printed track is overlaid by a track comprising a mixture of particles of silver and silver chloride.

* * * * *